United States Patent
Schiefer et al.

(10) Patent No.: US 8,778,262 B2
(45) Date of Patent: Jul. 15, 2014

(54) ALLOY HAVING REDUCED INCLUSIONS

(71) Applicant: Heraeus Precious metals GmbH & Co. KG, Hanau (DE)

(72) Inventors: Herwig Schiefer, Frankfurt (DE); Christoph Vogt, Hanau (DE); Heiko Specht, Hanau (DE); Jens Troetzschel, Neuwiedermus (DE)

(73) Assignee: Heraeus Precious Metals GmbH & Co. KG, Hanau (DE)

( * ) Notice: Subject to any disclaimer, the term of this patent is extended or adjusted under 35 U.S.C. 154(b) by 0 days.

(21) Appl. No.: 13/782,407

(22) Filed: Mar. 1, 2013

(65) Prior Publication Data

US 2013/0177470 A1    Jul. 11, 2013

Related U.S. Application Data

(62) Division of application No. 12/959,031, filed on Dec. 2, 2010, now Pat. No. 8,394,170.

(30) Foreign Application Priority Data

Dec. 20, 2009    (DE) .................. 10 2009 056 504

(51) Int. Cl.
  *C22C 30/00* (2006.01)
  *C22C 27/00* (2006.01)
  *A61F 2/02* (2006.01)

(52) U.S. Cl.
  USPC ............... 420/426; 623/11.11; 623/924

(58) Field of Classification Search
  USPC ............................................. 420/426
  See application file for complete search history.

(56) References Cited

U.S. PATENT DOCUMENTS

| 3,592,637 | A | 7/1971 | Brown et al. | |
| 5,374,295 | A | 12/1994 | Miura et al. | |
| 7,344,560 | B2 * | 3/2008 | Gregorich et al. | 623/1.15 |
| 2006/0153729 | A1 | 7/2006 | Stinson et al. | |
| 2010/0168841 | A1 | 7/2010 | Furst et al. | |
| 2011/0033335 | A1 | 2/2011 | Schiefer et al. | |
| 2011/0129386 | A1 | 6/2011 | Schiefer et al. | |
| 2011/0264161 | A1 | 10/2011 | Schiefer et al. | |

FOREIGN PATENT DOCUMENTS

| DE | C 5588 VI | 8/1956 | |
| DE | 691 26 973 | 11/1991 | |
| EP | 0801138 | 10/1997 | |
| EP | 1444993 A1 * | 8/2004 | A61L 27/04 |
| EP | 1444993 | 11/2004 | |
| JP | 359035642 | 2/1984 | |
| WO | 9118121 | 11/1991 | |
| WO | 2009079282 | 6/2009 | |

OTHER PUBLICATIONS

"Periodic Table: Melting Point" at http://www.chemicalelements.com/index.html. Created by Yinon Bentor. Copyright 1996-2009. Downloaded May 31, 2012.

(Continued)

*Primary Examiner* — George Wyszomierski
*Assistant Examiner* — Tima M McGuthry Banks
(74) *Attorney, Agent, or Firm* — Dicke, Billig & Czaja, PLLC (57) ABSTRACT

One aspect is an alloy consisting of niobium, zirconium, tantalum, and tungsten. The alloy is formed with a melt metallurgical route such that all four metals solidify as a homogeneous alloy having no inclusions more than 10 μm in size.

17 Claims, 5 Drawing Sheets

(56) References Cited

OTHER PUBLICATIONS

O'Brien, Barry et al., "Development of a New Niobium-Based Alloy for Vascular Stent Applications," Journal of the Mechanical Behavior of Biomedical Materials I, pp. 303-312 (2008).

The Restriction Requirement for U.S. Appl. No. 12/959,031 mailed May 16, 2012 (6 pages).

The Office Action for U.S. Appl. No. 12/959,031 mailed Jul. 17, 2012 (14 pages).

The Notice of Allowance for U.S. Appl. No. 12/959,031 mailed Nov. 8, 2012 (6 pages).

The Office Action for U.S. Appl. No. 12/851,892 mailed Jun. 5, 2012 (18 pages).

The Final Office Action for U.S. Appl. No. 12/851,892 mailed Sep. 20, 2012 (5 pages).

The Notice of Allowance for U.S. Appl. No. 12/851,892 mailed Dec. 6, 2012 (9 pages).

The Restriction Requirement for U.S. Appl. No. 13/091,852 mailed Feb. 26, 2013 (6 pages).

\* cited by examiner

ALLOY HAVING REDUCED INCLUSIONS

CROSS-REFERENCE TO RELATED APPLICATIONS

This application is a divisional of U.S. patent application Ser. No. 12/959,031, Now U.S. Pat.No. 8,394,170, entitled "USE OF POWDER-METALLURGICAL PRE-MATERIAL FOR PRODUCING AN NB ALLOY THAT IS FREE OF INCLUSIONS," having a filing date of Dec. 2, 2010, which claims priority to German Patent Application No. DE 10 2009 056 504.3, filed on Dec. 2, 2009, all of which are incorporated herein by reference.

This patent application is also related to patent application Ser. No. 12/851,892, now U.S. Pat. No. 8,414,679, filed on Aug. 6, 2010, entitled "PRODUCING AN ALLOY WITH A POWDER METALLURGICAL PRE-MATERIAL" and patent application Ser. No. 13/091,852, filed on Apr. 21, 2011, entitled "MELTING METHOD FOR PRODUCING AN INCLUSION-FREE TA-BASE ALLOY".

BACKGROUND

One aspect relates to a method for producing an alloy, whereby the alloy consists of a first metal, a second metal, a third metal, and a fourth metal, and the first metal, the second metal, the third metal, and the fourth metal are selected from the group consisting of the metals, niobium, zirconium, tantalum, and tungsten.

In medical technology, wires and tubes are needed for the production of medical components. Said wires and tubes are made, for example, of alloys of multiple high-melting metals. In "Journal of the mechanical behavior of biomedical materials I," (2008), p. 303-312, a method for producing an alloy from the metals, niobium, zirconium, tantalum, and tungsten—which shall be referred to as NbTaWZr hereinafter for simplicity reasons—is described. In the scope of said method, the four metals are each ground to form a powder and then melted. Despite the individual metals being ground first, it has proven to be a disadvantage of said method that individual inclusions may arise in which only one element of the four metals specified above is present.

In production methods, which are also known, rods made of pure metals are bundled and melted in a high vacuum, for example, by means of an electron beam. It has proven to be disadvantageous in the case of alloys made of tantalum, niobium, zirconium, and tungsten, that the element with the highest melting point is melted only incompletely. To some extent, larger lumps, for example, of tungsten, drop into the melt bath during the melting process without mixing with the other components of the alloy. Referred to as inclusions or mono-elemental regions, such non-melted lumps of one of the alloy metals lead to failure of the material at a later time, when the alloy is drawn into a wire. This can lead to fissures or cavities arising at said inclusions. Moreover, said inclusions render the processing more difficult. For example, the inclusions reduce the fatigue resistance and lead to corrosion of a wire made of the alloy.

For these and other reasons there is a need for the present invention.

SUMMARY

One aspect is a method for producing an alloy, whereby the alloy consists of a first metal, a second metal, a third metal, and a fourth metal, and the first metal, the second metal, the third metal, and the fourth metal are selected from the group consisting of the metals, niobium, zirconium, tantalum, and tungsten. The includes grinding the first metal to form a first metal powder and grinding the second metal to form a second metal powder; mixing the first metal powder and the second metal powder to form a first blended powder; generating a first blended body from the blended powder by means of a powder metallurgical route; generating the alloy by melting the first blended body and the remaining metals by means of a melt metallurgical route.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

Further advantages, features, and details of the invention are evident from the subclaims and the description in the following, in which several exemplary embodiments of the invention are described in detail making reference to the drawings. The features mentioned in the claims and the description can be essential for the invention both as such and in any combination thereof. In the figures:

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

One embodiment provides a method for producing an alloy from the metals, niobium, zirconium, tantalum, and tungsten, in which the disadvantages mentioned above are prevented, in particular to provide a method that reduces the maximal size of the inclusions as compared to known methods. In addition, a use of the alloy produced according to the method is proposed. Also, an implantable medical device is proposed. Features and details that are described in the context of the method shall also apply in the context of the implantable medical device and use, and vice versa.

One embodiment discloses a method for producing an alloy, which is characterized in that a) the first metal is ground to form a first metal powder and the second metal is ground to form a second metal powder;

b) the first metal powder and the second metal powder are mixed to form a first blended powder;

c) the blended powder is used to produce a first blended body by a powder metallurgical route;

d) the alloy is generated by melting the first blended body and the remaining metals by means of a melt metallurgical route.

One embodiment is based on combining two methods for producing an alloy. This allows the advantages of the powder metallurgical route and of the melt metallurgical route to be combined. Performing the two routes—powder metallurgical and melt metallurgical—to be illustrated in more detail below sequentially results in alloys whose inclusions are less than 4 μm in size. In the context of one embodiment, the terms, inclusion or mono-elemental region, shall are used to refer to a region in the alloy that comprises only one of the various metals of the alloy. This mono-elemental region consists of just one metal of the alloy and contacts the other metals of the alloy only on its outside surfaces. One advantage of the powder metallurgical route is that it allows for good homogenization and easy alloying to be achieved at low sintering temperatures. In one embodiment, these advantages are combined with the advantages of the melt metallurgical route, that is, the high level of purity of the alloy that can be achieved and the feasibility of alloying high-melting metals together.

In the context of one embodiment, the term, "powder metallurgical route," denotes a manufacturing process, in which a metal object is manufactured from a metal powder. The term, "powder metallurgical route," includes the following manufacturing processes: hot pressing, sintering, hot isostatic pressing. Hot pressing involves shaping and compacting a metal powder to form a metal object by exposure to a, for example, uni-axial, pressure and temperature. Sintering involves a heat treatment, in which an object consisting of metal powder is compacted. In hot isostatic pressing (HIP), a metal powder that has been filled into a mold is compacted to form a metal object with approximately 100% density (isostatic) by means of high pressure and high temperature.

Because of the high affinity for oxygen, it has proven to be advantageous to melt refractory metals under vacuum conditions. This allows pre-existing impurities to be removed and gas inclusions in metals to be prevented. In the context of one embodiment, the term, "melt metallurgical route," is used to refer to a manufacturing process, in which a metal object is melted by exposure to an energy source in a vacuum. The term, "melt metallurgical route," includes, for example, the following manufacturing processes: vacuum induction, electron beam melting, and arc melting. In vacuum induction, the metal object to be melted is melted in a crucible by means of induction under vacuum conditions and then poured into a water-cooled crucible. In electron beam melting, energy-rich electron beams are used under vacuum conditions to melt high-melting materials, which are then poured into an ingot mold with a floor, which can be lowered, and cooled walls. In arc melting, an arc is ignited between the metal object to be melted and an electrode by means of high voltage and under vacuum conditions, which causes the material to melt.

The special feature according to one embodiment is that the method utilizes a two-stage process. A powder metallurgical route is used first followed by a melt metallurgical route. One embodiment provides for at least the first and the second metal to each be ground and processed to form a blended powder. Said blended powder is then used by means of the powder metallurgical route as the base for producing the first blended body. In order to meet one of the objects specified above, that is, to prevent the presence of mono-elemental inclusions in the finished alloy, it has proven to be advantageous if the mixing of the first metal powder and the second metal powder proceeds as part of a homogenization step. Said homogenization step can, if applicable, also be part of the powder metallurgical route. This allows an even distribution of the second metal powder in the first metal powder to be attained. There are no powder regions formed, in which just one metal is present. Rather, what is attained by means of the homogenization step is that the mixing ratio of the two metal powders with respect to each other is maintained by the blended powder and/or the blended body. In this context, the term, "maintained," is understood to mean that the same distribution of the first metal powder with respect to the second metal powder exists in each spatial element within the blended powder and/or blended body as long as the volume of the region concerned is at least 125-fold larger than the volume taken up by a single grain of the first and/or second metal powder.

Any of the following methods, for example, can be applied in the scope of the homogenization step:

Use of pre-alloyed powder

Coating of powder or

Mechanical alloying

The use of pre-alloyed powder proceeds as follows: a NbTaWZr body produced by means of HIP is treated with hydrogen, which causes the body to become brittle. The body is then processed to form a powder by grinding. Subsequently, the powder is aged in a vacuum at a temperature >600° in order to remove the H from the metal. Then the powder can be compacted and sintered by the PM route. The following procedural steps result in the scope of homogenization by coating the powder: the main alloy component (for example, Nb powder particles) can be coated with a slurry (consisting of fine W powder and a binding agent). Subsequently, the coated powder particles are compacted and sintered jointly by the PM route. The steps involved in the scope of mechanical alloying are as follows: intensive mechanical treatment of the powder (grinding at high rotational speed with many grinding spheres) leads to local welding of individual powder particles to each other. The high temperature produced in the procedure leads to diffusion between the welded particles which increases the adhesion significantly. The powder thus obtained is then compacted and sintered according to PM methods.

One variant of a development of the method according to one embodiment is characterized in that at least three of the four metals are ground to form metal powders and mixed to form the first blended powder in steps a) and b). Said blended powder is processed to form a first blended body by means of the powder metallurgical route. In this context, the weight fractions of the three metal powders correspond to the alloying ratio desired later on. This variant of a development of the method according to one embodiment is characterized by its simplicity, since all it requires is grinding three metal powders. In step d), the alloy is produced by melting the first blended body made up of three metal powders and the remaining metal by means of the melt metallurgical route. As before, a homogenization step can be integrated in order to ensure that the first blended powder and/or the first blended body have an even distribution of the three metals.

A variant of a development that goes even further provides four metals to be mixed in the steps a) and b), whereby the alloy is produced in step d) by melting the first blended body by means of a melt metallurgical route. In said development of the method according to one embodiment, the method includes the steps of grinding the first metal to form a first metal powder, grinding the second metal to form a second metal powder, grinding the third metal to form a third metal powder, and grinding the fourth metal to form a fourth metal powder, mixing the first metal powder, the second metal powder, the third metal powder, and the fourth metal powder to form the first blended powder, whereby the alloy is produced in step d) by melting the first blended body by means of the powder metallurgical route. Said variant of a development of the method according to one embodiment is characterized in that all four metals are converted to powder form such as is already known in the prior art. However, unlike the prior art, a powder metallurgical route is used in order to ensure homogenization of the four metals in the first blended powder. Only by this means can mono-elemental inclusions, in which only one of the four requisite metals is present, can be prevented from arising in the finished alloy. As discussed, such mono-elemental regions quickly lead to corrosion and/or, if exposed to load for long periods of time, fatigue fracture of the alloy material.

Another development of the method according to one embodiment is characterized by i. grinding the third metal to form the third metal powder;
ii. generating a first additional body from the third metal powder by means of the powder metallurgical route;
prior to step d), and by the alloy being generated in step d) by concurrent melting of the first blended body, the first additional body, and the remaining metal by a melt metallurgical route. This variant of the method is characterized in that a first additional body is generated from the third metal, which first additional body is then melted in addition to the blended body in the scope of the melt metallurgical route. The remaining—that is, fourth—metal can be integrated into the melt metallurgical route as raw material in the form of a rod or a bar.

Another variant of the method is characterized by

I. grinding the fourth metal to form a fourth metal powder;
II. generating a second additional body from the fourth metal powder by means of the powder metallurgical route;
prior to step d), and by the alloy being generated in step d) by concurrent melting of the first blended body, the second additional body, and the remaining metal by a melt metallurgical route. This variant of the method is characterized in that a second additional body is generated from the fourth metal, which second additional body is then melted in addition to the blended body in the scope of the melt metallurgical route. The remaining—that is, third—metal can be integrated into the melt metallurgical route as raw material in the form of a rod or a bar. Moreover, the remaining metal can therefore be incorporated into the alloy as a first additional body in this case. In this context, three bodies generated by means of the powder metallurgical route—the first blended body, the first additional body, and the second additional body—would be subjected to a melt metallurgical treatment in order to generate the alloy. The use of three bodies that have been produced by means of the powder metallurgical route and contain the four claimed metals is advantageous in one embodiment, in that the grain size of the individual metals is reduced from the onset by the grinding alone. Accordingly, this results in a very even and homogeneous alloy.

Another variant of a development of the method according to the one embodiment is characterized by:

grinding the third metal to form a third metal powder and grinding the fourth metal to form a fourth metal powder;
mixing the third metal powder and the fourth metal powder to form a second blended powder;
generating a second blended body from the second blended powder by means of the powder metallurgical route;
after step c);
and generating the alloy in step d) by melting the first blended body and the second blended body by means of a melt metallurgical route.

Said embodiment of the method according to one embodiment includes the formation of two blended bodies. Both the first blended body and the second blended body are generated from a blended powder each by means of the powder metallurgical route. In this context, each blended powder contains two metals. Accordingly, the first and second blended bodies are generated concurrently by means of the powder metallurgical route. As discussed, a homogenization can be carried out in the scope of the powder metallurgical route. Said homogenization step ensures that the two metal powders contained in one blended powder each are distributed evenly and homogeneously.

Two metals whose melting temperatures are as similar as possible are ground to form a blended body. This ensures that the melting of the first and/or second blended body in the melt metallurgical route is even. In step d), the NbTaWZr alloy is then attained by melting the first blended body and the remaining metals, in the form of the second blended body, by means of the melt metallurgical route. This variant of the method surprisingly facilitates the production of particularly homogeneous alloys. Accordingly, tests have illustrated that the desired distribution of the alloy is present in a volume that is smaller than 125-fold the largest powder diameter. Accordingly, even the finest scales illustrate no deviation from the desired composition for the NbTaWZr alloy to be attained.

The first and second blended body are then melted jointly by means of the melt metallurgical route in the subsequent step d). This can proceed, for example, by bombardment with electrons in electron beam melting. In the process, the melted particles of the blended bodies flow into a water-cooled ingot mold and solidify therein as an alloy. In this variant of a development of the melt metallurgical route, the blended bodies are arranged next to each other such that both are hit by the electron beam and are thus melted concurrently. Said concurrent use of the melt metallurgical route ensures that melted particles of all four metals flow into the ingot mold and solidify therein as a homogeneous alloy whose inclusions are less than 10 µm in size. Said alloys can then be used, for example, for implantable medical devices. In the scope of the variant of the method according to one embodiment described here, the first blended powder can just as well be compacted by hot isostatic pressing (HIP). Subsequently, the HIP body is cut into oblong bars which are melted jointly with the second blended body and combined to form an alloy by means of the melt metallurgical route.

A variant of a development of the method according to one embodiment is characterized by the alloy comprising the following fractions of the metals:

0.5 wt-% to 10 wt-% zirconium,
0.5 wt-% to 9 wt-% tungsten,
20 wt-% to 40 wt-% tantalum, and
the remainder being the niobium fraction;

by the alloy, for example, comprising the following fractions of the metals:

0.5 wt-% to 2.3 wt-% zirconium,
2.5 wt-% to 4.5 wt-% tungsten,
24 wt-% to 32 wt-% tantalum, and
the remainder being the niobium fraction, for example, by the alloy comprising the following fractions of the metals:

1.3 wt-% zirconium,
3.5 wt-% tungsten,
28 wt-% tantalum, and
the remainder being the niobium fraction.

According to one embodiment, the alloy consists of the four metals, niobium, zirconium, tantalum, and tungsten. It is self-evident that this alloy also includes the inevitable impurities. Although the alloy is to consist of the four specified metals in the end, inevitable impurities of the four metals cannot be prevented in the scope of the production process. Said inevitable impurities should obviously also become part of the alloy with the aim being to keep them as low as possible. It has therefore proven to be preferred in one embodiment to use the four metals at the following purities:

zirconium more pure than 99.9%, in particular more pure than 99.95%, particularly preferred more pure than 99.995%,
tungsten more pure than 99.9%, in particular more pure than 99.95%, particularly preferred more pure than 99.995%,
tantalum more pure than 99.9%, in particular more pure than 99.95%, particularly preferred more pure than 99.995%,
niobium more pure than 99.9%, in particular more pure than 99.95%, particularly preferred more pure than 99.995%.

Reduction of the impurities to the levels specified above allows alloys to be produced that are biocompatible. Said biocompatible alloys are well-suited for use for implantable medical devices.

Another development is characterized by the first metal being tantalum, the second metal being tungsten, the third metal being niobium, and the fourth metal being zirconium. In the context of the method for producing two blended bodies from two blended powders as described above, it has proven to be advantageous in one embodiment to produce the first blended powder from the metals, tantalum and tungsten. Accordingly, the second blended powder is made up by niobium and zirconium. Tantalum and tungsten have similar melting points and can be homogenized. Accordingly, this results in a particularly even alloy which comprises no mono-elemental inclusions.

In order to attain particular purity of the alloy and to further reduce the size of any inclusions, it has proven to be advantageous in one embodiment to supplement the method to the effect that the method, after step d), comprises the step of e) melting the alloy by means of the melt metallurgical route.

In the scope of procedural step e), the alloy generated in step d) is melted again. After the alloy generated in step d) has solidified, it can be melted again by means of the melt metallurgical route. Accordingly, it is conceivable, for example, to melt the alloy from step e) in a vacuum using an electron beam. Any inclusions, which already are less than 4 μm in size, can be further reduced in size by the repeated melting. A further development of said variant of a development provides for step e) to be carried out multiply. Accordingly, it has proven to be advantageous in one embodiment to perform step e) two to ten times, and in one embodiment three to five times. Repeated melting of the alloy by means of the melt metallurgical route further reduces the size of the inclusions. Accordingly, it has been possible to realize inclusion sizes of clearly less than 1 μm, in one embodiment less than 0.2 μm, by means of melting three to five times in the scope of step e). Alloys with inclusions of this size can be used to advantage in one embodiment, for implantable medical objects. Inclusions of this size have a negligible influence on the fatigue resistance of the finished product.

Another variant of a development of the method according to one embodiment is characterized in that the first metal is ground to form the a first metal powder with a first powder particle size of between 4 μm and 0.1 μm and/or the second metal is ground to form the second metal powder with a second powder particle size of between 4 μm and 0.1 μm, in one embodiment between 4 μm and 1 μm. In the scope of the method, both the first and the second metal each are ground to form metal powder. Depending on the development of the embodiment, the third metal also can be ground to form a third metal powder and/or the fourth metal can be ground to form a fourth metal powder. In order to ensure that the inclusions, that is, those regions in the alloy, in which only a single metal is present in elemental form, are small in size, the metals must be ground fine enough during the preparation phase for the powder particle size of the individual metal powders to be between 4 μm and 0.1 μm, in one embodiment between 4 μm and 1 μm, since the size of the powder particles is correlated to the size of the inclusions. In the context of one embodiment, the term, "powder particle size," is used to refer to the maximal size of those particles of the metal powder that is attained in the scope of grinding and ensuing screening. Accordingly, the size of the mesh of the sieve used to screen the metal powder after grinding indicates the upper limit of the powder particle size. According to one embodiment, the required powder particle size shall specify the maximal size of a particle of the metal powder. No particle of the metal powder shall be of a size larger than the powder particle size, but can be of any smaller size.

Due to the grinding of the first metal and second metal, and in one embodiment, of the third metal and/or fourth metal also, the size of the inclusions of the first and/or second and/or third metal and/or fourth metal in the alloy is between 10 μm and 10 nm. If, in addition, step e) according to one embodiment is performed multiply, it is feasible according to one embodiment for the size of the inclusions to be between 4 μm and 20 nm, and in one embodiment between 2 μm and 50 nm. Said size is non-objectionable for the use in alloys of implantable medical devices.

A use in an implantable medical device of an alloy that was manufactured according to any one of the methods described above is also claimed. The method according to one embodiment enables the production of an alloy that is particularly well-suited for implantable medical devices, in one embodiment, since no non-melted lumps of an alloy metal—also called mono-elemental region—arise. Rather, all alloy metals are melted such that no mono-elemental regions arise that might lead to fissures or cavities in implantable medical devices that are made up of an alloy that is produced according to one embodiment. An implantable medical device that is characterized by the implantable medical device being, at least in part, made up by an alloy is also claimed, whereby the alloy is produced according to any one of the methods described above. It has proven to be a preferred variant of a development of said implantable medical device according to one embodiment, that the implantable medical device is a stent or a precursor product of a stent or an electrode or a cardiac pacemaker casing or a cable or an electrical lead. All medical devices mentioned above have diameters or wall thicknesses that are on the same order of magnitude as the size of non-melted lumps of an alloy metal in known production procedures. Accordingly, fissures or cavities arise in medical devices according to the prior art if they are produced from said alloys according to known methods. The same is not true if the medical device is made up of an alloy that is produced according to the methods according to one embodiment.

An issue, on which the method according to one embodiment for producing an alloy is based, is that not all metals are distributed evenly in the finished alloy, for example, in the case of high-melting refractory metals, but rather regions— also called inclusions or mono-elemental regions—are formed, in each of which only one metal of the various metals used for the alloy is present in pure form. Inclusions of this type can significantly reduce the fatigue resistance of the finished product. In order to overcome this disadvantage, one embodiment discloses a method for producing an alloy from the refractory metals, niobium, zirconium, tantalum, and tungsten, whereby the alloy 100 comprises a first metal 10, a second metal 20, a third metal 30, and a fourth metal 40. In this context, a fusion of said metals 10, 20, 30, 40 to form a combination metal is referred to as alloy 100. The special feature according to one embodiment is that first a powder metallurgical route and subsequently a melt metallurgical route is used sequentially, that is, one after the other, for producing the alloy.

Figure 1:
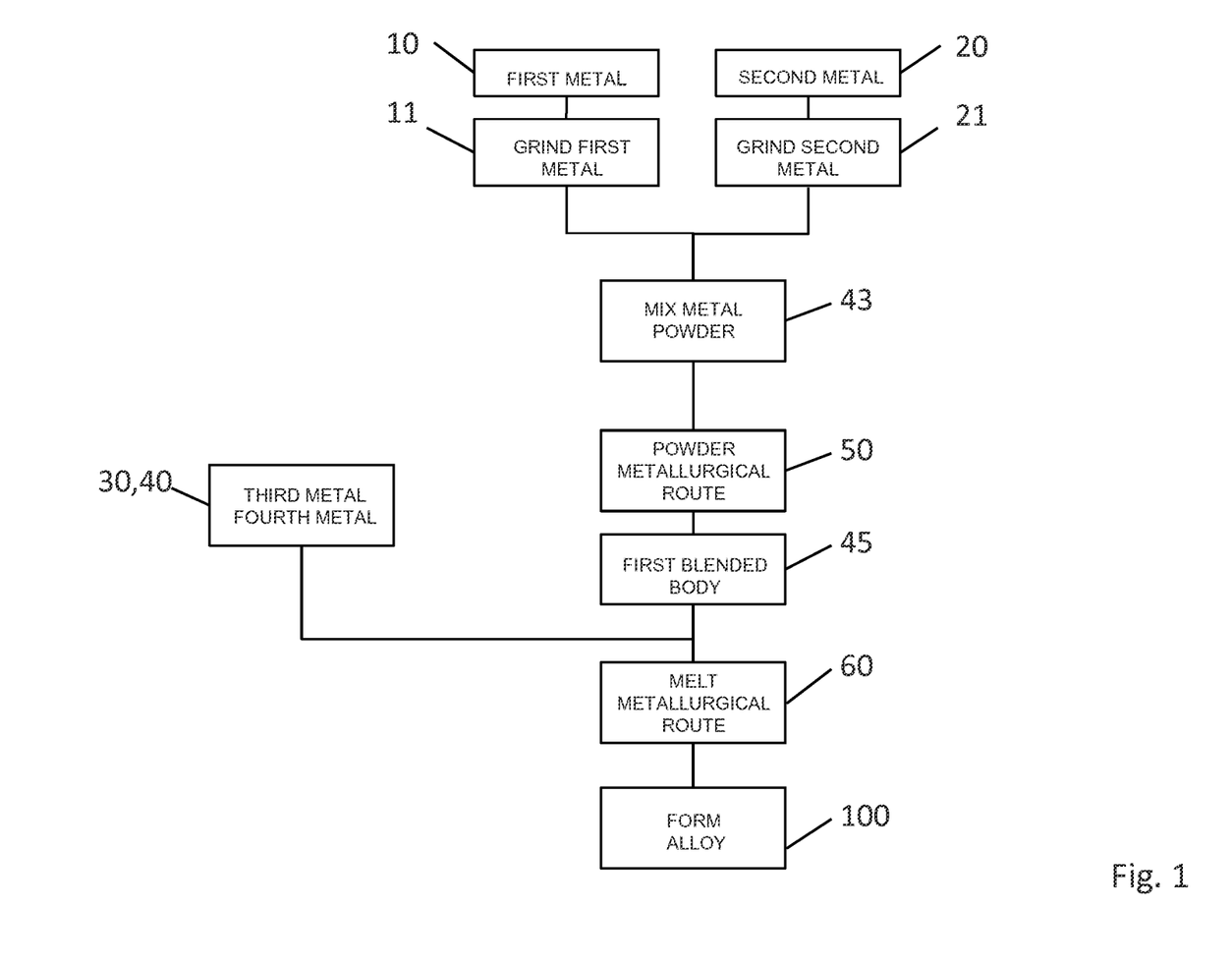
FIG. 1 illustrates a flow diagram of the method according to one embodiment.

FIG. 1 illustrates a flow diagram illustrating the method according to one embodiment for producing the alloy 100. The first metal 10 and the second metal 20 are used as the basis in this context. Firstly, the first metal 10 is ground to form a first metal powder 11. Concurrently or subsequently, the second metal 20 can be ground to form a second metal powder 21. In this context, it has proven to be advantageous for the first metal 10 to be ground to form a first metal powder 11 with a particle size between 10 µm and 0.1 µm. The same applies to the second metal that is ground to form a second metal powder 21. Subsequently, the first metal powder 11 and the second metal powder 21 are mixed to form a first blended powder 43. Said first blended powder 43 comprises the first metal powder 11 and the second metal powder 21 with their distribution corresponding to the one which the two metals 10, 20 are to possess later in the alloy 100. The blended powder 43 is used to generate a first blended body 45 by means of the powder metallurgical route 50. The powder metallurgical route 50 can, for example, be a process of hot isostatic pressing (HIP). In the process, the first blended powder 43 is compacted to form the blended body 45 by the influence of pressure and heat. Subsequently, the first blended body 45 can be cut into oblong bars, which are then melted by means of the melt metallurgical route 60 in order to form the alloy 100. The melt metallurgical route also includes melting of the remaining metals, 30, 40. Accordingly, the alloy 100 is generated by melting the first blended body 45 and the remaining metals 30, 40 by means of the melt metallurgical route. The bodies of the remaining metals can be a bar or a rod that comprises the respective metal in pure form. Said bodies of the third and fourth metals 30, 40 are bundled with the first blended body 45 at a ratio which corresponds to the later ratio of the metals 10, 20, 30, 40 in the alloy 100.

In the context of one embodiment, the term, powder metallurgical route, shall in particular refer to the manufacturing of a product using the following steps, whereby each step can take a different form:

1) generating a metal powder 11, 21,
2) shaping, and
3) heat treatment.

For manufacturing an alloy 100 by means of the powder metallurgical route 50, metal powders of the metals having powder particle sizes between 10 µm and 0.1 µm are needed. The type of powder production has a major impact on the properties of the powders. Mechanical methods, chemical reduction methods or electrolytic methods as well as the carbonyl methods, spinning, atomizing, and other methods can be used for producing the powder. The shaping involves compaction of the metal powder in pressing tools under high pressure (between 1 and 10 t/cm$^2$ (tons per square centimeter) to form green compacts. Other feasible methods include compaction by vibration, slip casting method, casting methods and methods involving the addition of binding agents. In heat treatment (also called sintering), the powder particles are solidly bonded at their contact surfaces by diffusion of the metal atoms. The sintering temperature of single-phase powders is between 65 and 80% of the solidus temperature.

Figure 2:
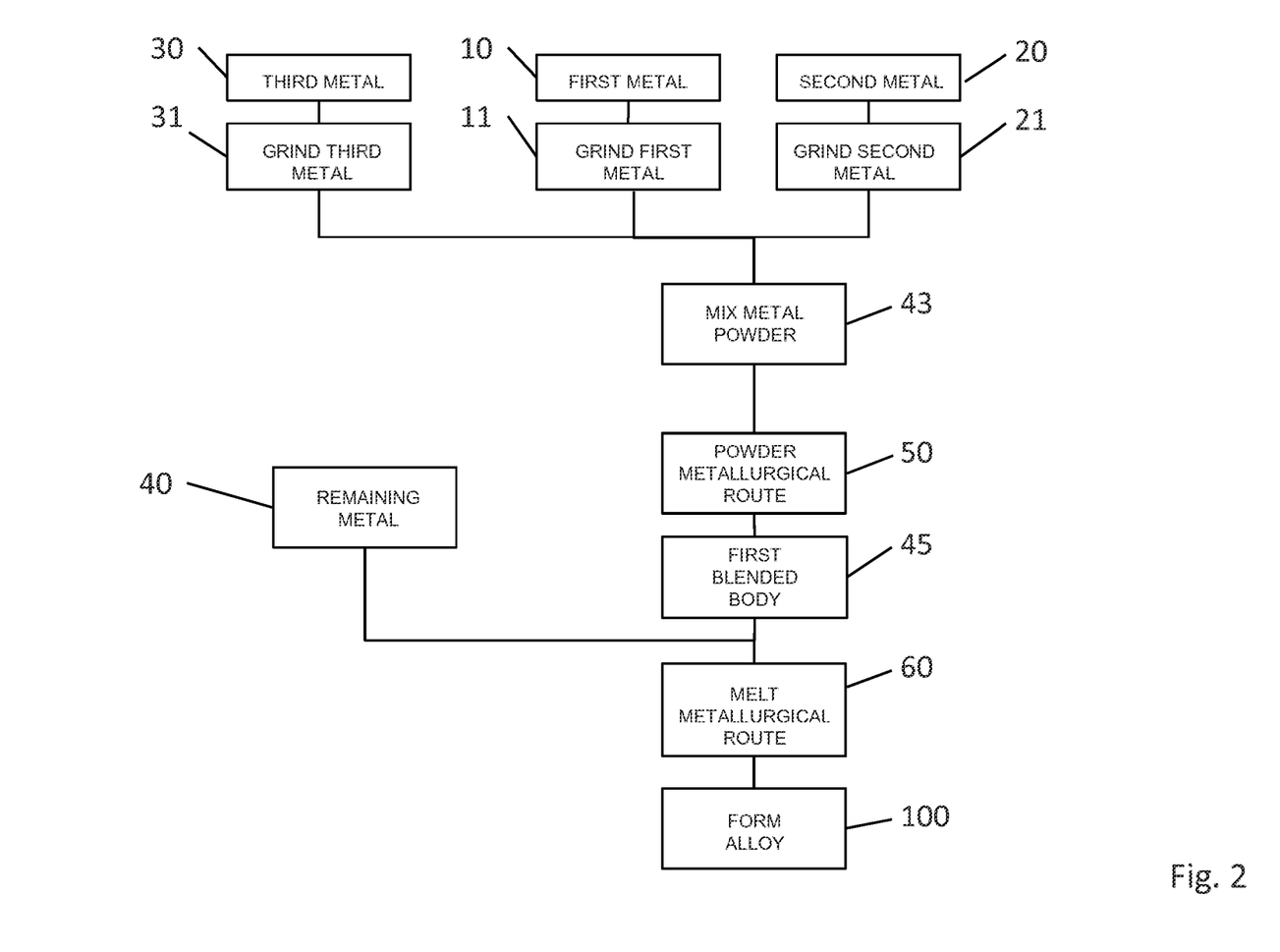
FIG. 2 illustrates a flow diagram of a first development of the method according to one embodiment.

FIG. 2 illustrates another development of the method according to one embodiment. In a first step, the three metals 10, 20, 30 each are separately ground to form a first metal powder 11, second metal powder 21, and third metal powder 31. Subsequently, the first metal powder 11, second metal powder 21, and third metal powder 31 are mixed to form the first blended powder 43. Then the blended body 45 is manufactured from the blended powder 43 by means of a powder metallurgical production process 50. A homogenization step can also be carried out in the scope of the powder metallurgical route 50 and is utilized to ensure that the distribution of the individual metal powders in the blended powder 43 is as even as possible. Subsequently, the first blended body 45 and the remaining metal 40—that is, the fourth metal—are melted by means of the melt metallurgical route 60. This results in the desired alloy 100. Said alloy 100 can be subjected to the melt metallurgical route 60 again in order to attain further reduction of the size of any mono-elemental regions that may still be present. Said mono-elemental regions can then be of a size of less than 0.5 µm, one embodiment less than 0.1 µm.

Figure 3:
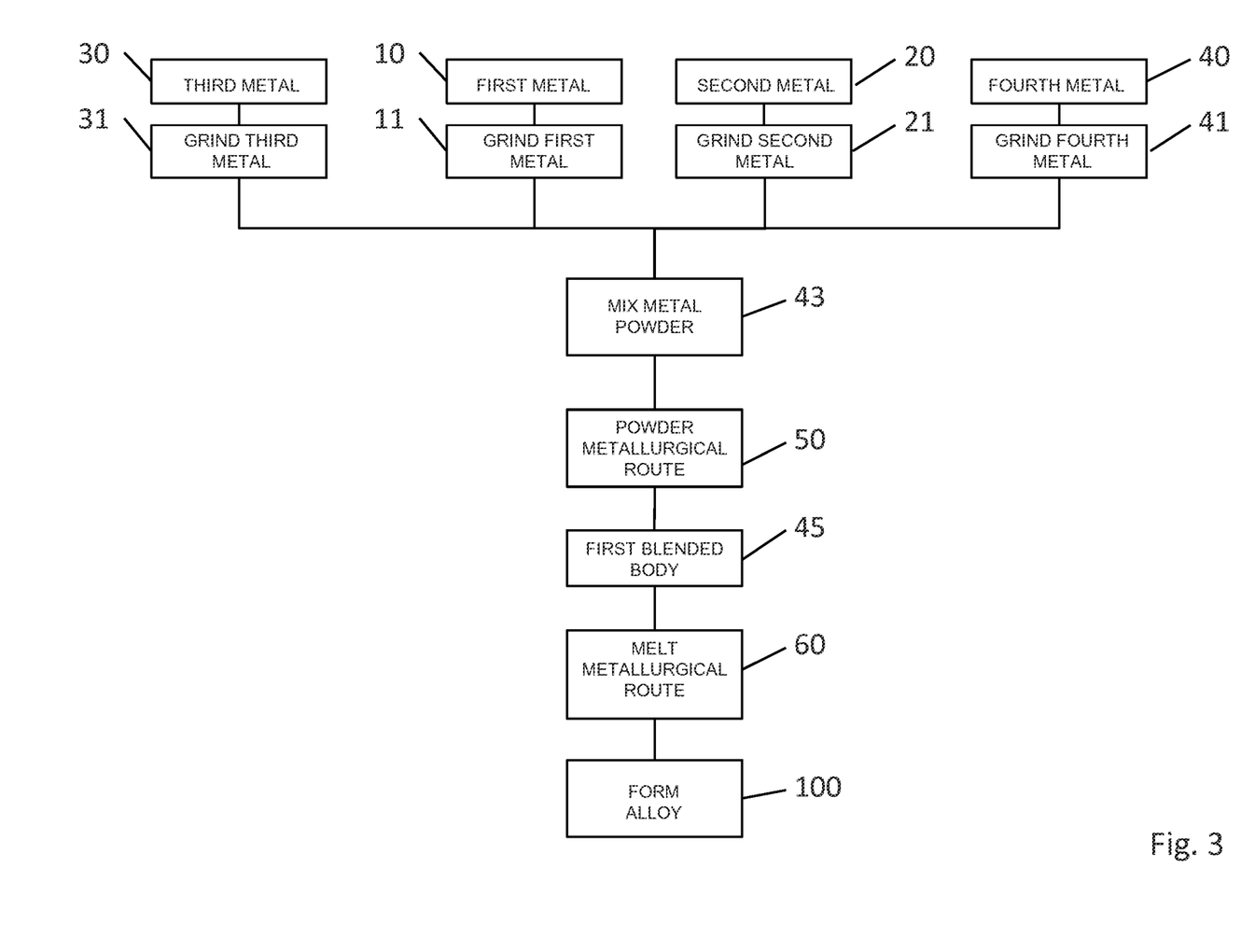
FIG. 3 illustrates another development of the method according to one embodiment.

FIG. 3 illustrates a variant of a development of the method according to one embodiment. Said variant of a development is characterized by grinding the first metal 10 to form a first metal powder 11, grinding the second metal 20 to form a second metal powder 21, grinding the third metal 30 to form a third metal powder 31, and grinding the fourth metal 40 to form a fourth metal powder 41;

mixing the first metal powder 11, second metal powder 21, third metal powder 31, and fourth metal powder 41 to form the first blended powder 43;

whereby, the alloy 100 is generated in step d) by melting the first blended body 45 by means of the melt metallurgical route 60. Accordingly, all four metals 10, 20, 30, 40 are processed to form a first blended body 45 in this variant of a development. The scope of generating the first blended body 45 by means of the powder metallurgical route 50 includes a homogenization for production reasons, in contrast to the prior art. The homogenization can be intensified by the homogenization step mentioned above. It is thus ensured that no mono-elemental regions arise in the finished alloy 100 which might lead to fissures and/or damage during the use of the alloy 100 as base material of an implantable medical device, which would impair the serviceability of the implantable medical device. As discussed above, the alloy 100 is generated by means of the melt metallurgical route 60 after the first blended body 45 is generated.

Figure 4:
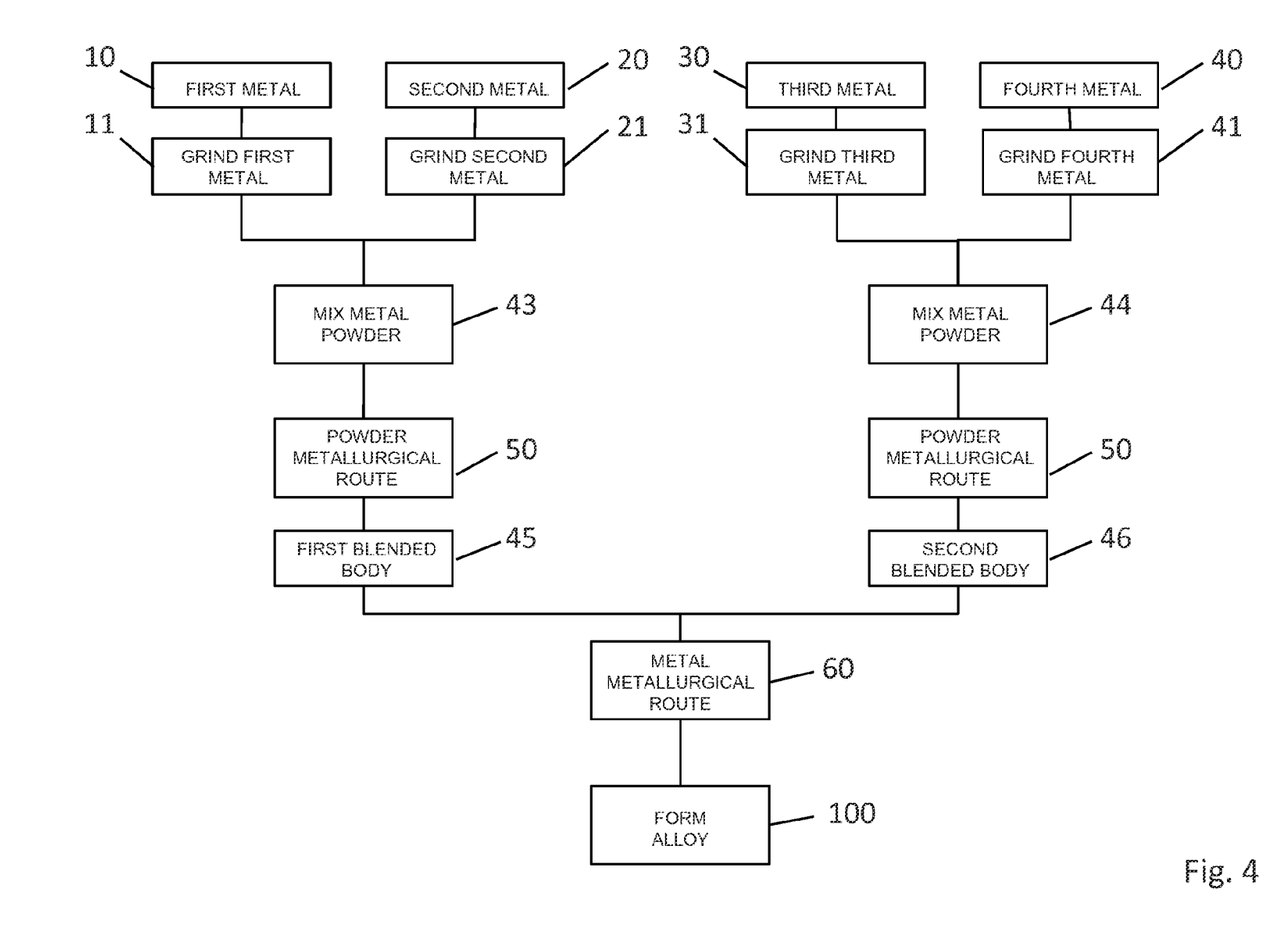
FIG. 4 illustrates a flow diagram of another embodiment of the method according to one embodiment.

Another development of the method according to one embodiment is illustrated in FIG. 4 and is characterized in that the first metal 10 and the second metal 20 each are ground to form metal powders 11, 21 and subsequently mixed to form a first metal powder 43. Said first metal powder 43 is then used as the basis for generating the first blended body 45 by means of the powder metallurgical route. Subsequently or concurrently, the third metal 30 and the fourth metal 40 are ground to form a third metal powder 31 and a fourth metal powder 41, respectively. Said two metal powders 31, 41 are also mixed to form a second blended powder 44. A homogenization can also proceed, as before. Subsequently and/or partly concurrent with the homogenization step, the powder metallurgical route 50 is applied. A second blended body 46 is obtained on the basis of the second blended powder 44. Said two blended bodies 45, 46 each contain the powders of the individual metals 10, 20, 30, 40 at the same ratio as desired to be present later in the alloy. The two metal powders are mixed such that the two highest-melting metals are integrated into the first metal powder 43. Accordingly, it is expedient to combine tantalum and tungsten in the first blended powder 43. Accordingly, the second blended powder 44 contains niobium and zirconium which have comparable melting temperatures. Accordingly, a starting base that is even and can be converted into the later alloy is thus created. Subsequently, the alloy 100 is generated in step d) by means of the melt metallurgical route 60 by melting the first blended body 45 and the remaining metals 30, 40 in the form of the second blended body 46. It has proven to be advantageous in one embodiment for alloy 100 to comprise the following fractions of the metals 10, 20, 30, 40: 0.5 wt-% to 10 wt-% zirconium, 0.5 wt-% to 9 wt-% tungsten, 20 wt-% to 40 wt-% tantalum, and the remainder being accounted for by the niobium fraction, in particular for the alloy 100 to comprise the following fractions of the metals 10, 20, 30, 40: 1.3 wt-% zirconium, 3.5 wt-% tungsten, 28 wt-% tantalum, and the remainder being accounted for by the niobium fraction.

Figure 5:
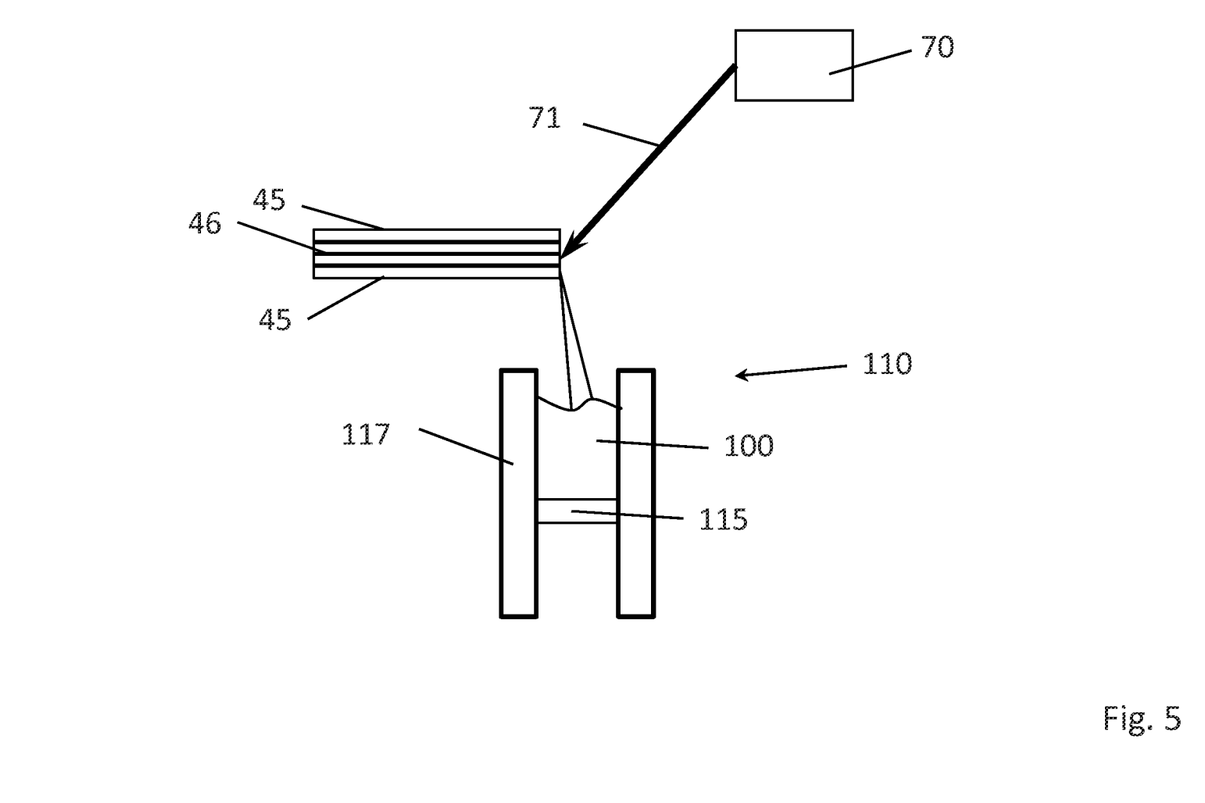
FIG. 5 illustrates a schematic view of a melt metallurgical processing within the scope of the method according to one embodiment.

The purpose of FIG. 5 is to illustrate the melt metallurgical route 60 by means of an electron beam melting process. As has been discussed above, a second blended body 46 can be generated from the third metal 30 and the fourth metal 40 by means of the powder metallurgical route 50. Said blended body 46 is then arranged spatially next to the first blended body 45 in a vacuum chamber. An electron source 70 generates an electron beam 71 that knocks single metal particles from the first and second blended bodies 45, 46. In this context, the first, second, third, and fourth metals 10, 20, 30, 40 should be ground to a powder particle size between 10 μm and 0.1 μm for the inclusions of the first metal 10 and/or the second metal 20 and/or the third metal 30 and/or the fourth metal 40 in the alloy to be between 4 μm and 10 nm in size. The melted metal particles flow into the ingot mold 110 where they form the alloy 100. For the alloy 100 to solidify quickly, the walls 117 of the ingot mold are cooled. A floor 115 that can be lowered ensures that the path to be traveled by the melted metal particles until they impact the surface of the alloy 100 is always the same.

A development of the method according to one embodiment provides the alloy 100 to be melted again after step d) by means of the melt metallurgical route 60. Multiple melting of the alloy 100 by means of the melt metallurgical route 60 allows the size of the inclusions of the first metal 10 and/or the second metal 20 and/or the third metal 30 and/or the fourth metal 40 in the alloy to be reduced further. It has proven to be advantageous in one embodiment to melt the alloy 100 three to five times by melt metallurgical means after generating it. In the process, it is feasible to attain inclusions of the first metal 10 and/or the second metal 20 and/or the third metal 30 and/or the fourth metal 40 that are between 4 μm and 20 nm in size. Inclusions of this type have negligible impacts on the fatigue resistance of the alloy in implantable medical devices.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. An alloy consisting of niobium, zirconium, tantalum, and tungsten, wherein the alloy is formed with a melt metallurgical route such that all four metals solidify as a homogeneous alloy having no inclusions more than 10 μm in size and characterized in that the alloy comprises no mono-element inclusions.

2. The alloy of claim 1 characterized in that formation of the alloy employs the powder metallurgical and melt metallurgical routes sequentially such that the alloy has no inclusions more than 4 μm in size.

3. The alloy of claim 1 characterized in that formation of the alloy employs melting the alloy by means of the melt metallurgical route at least three times such that the alloy has no inclusions more than 0.2 μm in size such that the inclusion have negligible influence on fatigue resistance of the alloy.

4. The alloy of claim 1 characterized in that formation of the alloy employs grinding of each of the niobium, zirconium, tantalum, and tungsten such that all inclusions in the alloy are between 10 μm and 10 nm.

5. The alloy of claim 1 characterized in that formation of the alloy employs multiple melt metallurgical routes such that all inclusions in the alloy are between 10 μm and 10 nm.

6. The alloy of claim 5 characterized in that formation of the alloy employs multiple melt metallurgical routes such that all inclusions in the alloy are less than 0.1 μm.

7. The alloy of claim 1 characterized by the alloy comprising the following fractions of the metals:
  0.5 wt-% to 10 wt-% zirconium,
  0.5 wt-% to 9 wt-% tungsten,
  20 wt-% to 40 wt-% tantalum, and
  the remainder being accounted for by the niobium fraction.

8. The alloy of claim 1 characterized by the alloy comprising the following fractions of the metals:
  0.5 wt-% to 2.3 wt-% zirconium,
  2.5 wt-% to 4.5 wt-% tungsten,
  24 wt-% to 32 wt-% tantalum, and
  the remainder being the niobium fraction.

9. The alloy of claim 1 characterized by the alloy comprising the following fractions of the metals:
  1.3 wt-% zirconium,
  3.5 wt-% tungsten,
  28 wt-% tantalum, and
  the remainder being accounted for by the niobium fraction.

10. An implantable medical device, characterized by the implantable device being made up, at least in part, of an alloy consisting of niobium, zirconium, tantalum, and tungsten, wherein the alloy is formed with a melt metallurgical route and a melt metallurgical route such that all four metals solidify as a homogeneous alloy having no inclusions more than 10 μm in size and characterized in that the alloy comprises no mono-elemental inclusions.

11. The implantable medical device of claim 10 characterized in that formation of the alloy employs the powder metallurgical and melt metallurgical routes sequentially such that the alloy has no inclusions more than 4 μm in size.

12. The implantable medical device of claim 10 characterized in that formation of the alloy employs melting the alloy by means of the melt metallurgical route at least three times such that the alloy has no inclusions more than 0.2 μm in size such that the inclusion have negligible influence on fatigue resistance of the alloy.

13. The implantable medical device of claim 10 characterized in that formation of the alloy employs grinding of each of the niobium, zirconium, tantalum, and tungsten such that all inclusions in the alloy are between 10 μm and 10 nm.

14. The implantable medical device of claim 10 characterized in that formation of the alloy employs multiple melt metallurgical routes such that all inclusions of the alloy are between 10 μm and 10 nm.

15. The implantable medical device of claim 10 characterized by the alloy comprising the following fractions of the metals:

0.5 wt-% to 10 wt-% zirconium,
0.5 wt-% to 9 wt-% tungsten,
20 wt-% to 40 wt-% tantalum, and
the remainder being accounted for by the niobium fraction.

16. The implantable medical device according to claim 10 characterized by the implantable medical device being a stent or a precursor product of a stent or an electrode or a cardiac pacemaker casing or a cable or an electrical lead.

17. An alloy consisting of a first metal, a second metal, a third metal, and a fourth metal, characterized in that the first metal, the second metal, the third metal, and the fourth metal are selected from the group consisting of the metals, niobium, zirconium, tantalum, and tungsten; and such that all four metals solidify as a homogeneous alloy having no inclusions more than 10 μm in size; and characterized in that the alloy is generated by:
grinding a first metal to form a first metal powder and grinding a second metal to form a second metal powder;
mixing the first metal powder and the second metal powder to form a first blended powder;
generating a first blended body from the blended powder by means of a powder metallurgical route; and
generating the alloy by melting the first blended body and a third metal and a fourth metal by means of a melt metallurgical route; and
characterized in that the alloy comprises no mono-elemental inclusions.

* * * * *